United States Patent [19]

Morris

[11] Patent Number: 4,820,490
[45] Date of Patent: Apr. 11, 1989

[54] DEVICE AND METHOD FOR CHEMICAL ANALYSIS OF FLUIDS WITH A REAGENT COATED LIGHT SOURCE

[75] Inventor: David A. N. Morris, Elkhart, Ind.

[73] Assignee: Miles Inc., Elkhart, Ind.

[21] Appl. No.: 75,844

[22] Filed: Jul. 20, 1987

Related U.S. Application Data

[62] Division of Ser. No. 906,086, Sep. 11, 1986, Pat. No. 4,717,545.

[51] Int. Cl.[4] ............ G01N 21/25; G01N 1/48; G01J 3/511
[52] U.S. Cl. .................... 422/58; 422/56; 436/805; 356/409; 356/420
[58] Field of Search ............ 436/805, 806; 422/58, 422/56; 356/409–415, 420

[56] References Cited

U.S. PATENT DOCUMENTS

| | | | |
|---|---|---|---|
| 4,050,895 | 9/1977 | Hardy et al. | 422/86 |
| 4,200,110 | 11/1977 | Peterson et al. | 422/58 |
| 4,560,248 | 8/1982 | Cramp et al. | 422/58 |
| 4,682,895 | 9/1985 | Costello | 436/164 |
| 4,717,545 | 9/1986 | Morris | 436/805 |

Primary Examiner—Sidney Marantz
Assistant Examiner—Lyle Alfandary-Alexander
Attorney, Agent, or Firm—Roger N. Coe

[57] ABSTRACT

A device for measuring transmittance of light comprises a light source, photodetector and signal processor. The concentration of a substance in a fluid sample can be accurately determined by coating the light source with a reagent that is chemically reactive with the substance and measuring light transmitted from the coating before and after the substance is applied to the coating. The coating can contain a solid support matrix, such as a translucent nonwoven paper web of the type used in reagent test strips and similar indicator devices. The invention is useful for making clinical analyses on body fluids.

12 Claims, 3 Drawing Sheets

DEVICE AND METHOD FOR CHEMICAL ANALYSIS OF FLUIDS WITH A REAGENT COATED LIGHT SOURCE

This is a division of application Ser. No. 906,086, filed 9/11/86, now U.S. Pat. No. 4,717,545.

BACKGROUND OF THE INVENTION

This invention relates to a method and a device for measuring light transmittance. More particularly, this invention relates to the qualitative or quantitative analysis of body fluids by measuring light transmitted from a coating, such as a reagent coated on the light emitting surface of a lamp. The invention is useful for detecting the presence of one or more constituents of a liquid test sample.

The spectral characteristics of light reflected and transmitted by a specimen are related to the chemical and physical characteristics of the specimen. With the advent of instrumental analysis, absorption of light by a specimen under test has become a widely used basis for biochemical assay procedures. For example, a reagent test strip used for qualitative and quantitative analysis can be contacted for a prescribed period of time with a body fluid, such as blood or urine. Light is projected onto the strip and light reflected by the strip is photoelectrically measured. The reflectance spectrum of the test strip will vary depending upon the concentration of the target substance in the body fluid being examined. Thus, by measuring the reflected light and computing the resulting reflectance, the desired analysis can be made by comparison with a standard based on a correlation of reflectance to concentration.

A reagent test strip is typically a test paper treated with various chemical reagents. Since the surface of the test strip does not have a uniform topography, it is difficult to make accurate and reproducible reflectance measurements because the result may depend upon where the measurement is made on the strip or on measurement geometry. In addition, some illumination from the light source is dissipated or lost. Thus, in order to obtain reflected energy of a desired magnitude, the magnitude of the illumination must be correspondingly increased to compensate for the light dissipated in the device. This can require a larger light source and the generation of heat in larger amounts and can lead to increased power consumption.

It has also been found with reagent test strips that the reflectance measurement is sensitive to the orientation of the strip in the test strip holder. For example, slight twisting or inclination of the specimen affects the magnitude of the reflectance measurement. In addition, it has been found that the reflectance measurement can be affected by the distance between the test strip and the light source.

Thus, there exists a need in the art for a method and a device for making rapid, accurate and reproducible optical measurements on a specimen under test. The device should employ direct illumination of the specimen. The device should minimize the amount of illumination dissipated or lost between the light source and the specimen in order to minimize power consumption. The device should provide optical measurements that are insensitive to subtle changes in the orientation of the specimen in the specimen holder and not susceptible to variations in the distance between the light source and the specimen.

SUMMARY OF THE INVENTION

Accordingly, this invention aids in fulfilling these needs in the art by providing a device for determining the presence or concentration of a substance in a medium by measuring light. The device comprises light source means for providing illumination and light responsive means for generating an electrical signal in response to light. Means are provided for measuring the electrical signal from the light responsive means. The light source has a surface through which or from which light passes. The surface has a coating thereon and the coating is chemically reactive with the substance being determined. Light from the light source passes through the surface and through or from the coating to the light responsive means. The amount of light transmitted through the coating after reaction with the substance being determined is a measure of the concentration of the substance in the coating. A light emitting diode (LED) is well suited for use as the light source.

This invention also provides a light-emitting diode having a light-emitting surface and a light-transmitting, liquid permeable coating on the surface. The coating contains a reagent composition for a ligand contained in a body fluid. Light from the diode illuminates the coating, and light transmitted from the coating changes after the ligand and reagent composition chemically react.

In addition, this invention provides a method for determining the presence or concentration of a ligand in a specimen by measuring transmission of light in a device comprising light source means for illuminating the specimen and means for measuring light from the specimen. The method comprises providing a transparent or translucent coating on a surface of the light source through which light from the light source passes. The coating contains a reagent that is chemically reactive with the ligand. Light from the light source transmitted from the coating to the measuring means is measured. A liquid containing the ligand is then applied onto the coating. The ligand and reagent are reacted for a time sufficient to react to form a reaction product. Light from the light source transmitted to the measuring means from the coating containing the reaction product is measured. The values obtained can then be compared with a standard.

It has been found that very accurate and reproducible optical measurements can be made on a specimen with this device and the procedure described. The measurement of light transmitted is not sensitive to slight changes in the orientation of the specimen in a specimen holder since the specimen is coated on the light source. In addition, the measurement is not susceptible to changes in the distance between the specimen and the light source as in prior art devices.

BRIEF DESCRIPTION OF THE DRAWINGS

This invention will be more fully understood by reference to the drawings in which.

DETAILED DESCRIPTION

The present invention deals with an assay for detecting a ligand in, or the ligand binding capacity of, a ligand sample in a coating. The coating thus functions as the specimen under test. The coating can include one or more reagent layers, wherein the reagent is responsive to the ligand in the sample or responsive to the ligand binding capacity of the sample to give a detectable response. Alternatively, the coating can contain the ligand to which the reagent responsive to the ligand is to be added. A support matrix can be included in the coating. Other layers can also be present, such as spreading layers, radiation diffusing or blocking layers, and the like.

The device and method of this invention measure light transmitted from or through the coating. The device is operated by supporting the coating in a fixed position while a light source is energized for a period of sufficient duration to illuminate the coating. Energy in the form of light transmitted from or through the coating is measured with a photodetector. The energy is then converted to an electrical signal and electronically processed to compare the signal with a reference level and for converting the result to a desired parameter, such as the concentration of protein in a blood sample under test.

Figure 1:
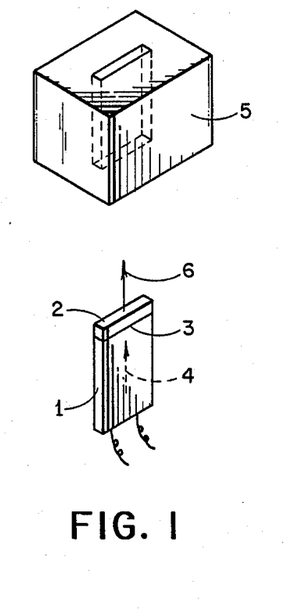
FIG. 1 is a perspective view of a coated LED of the invention.
Figure 2:
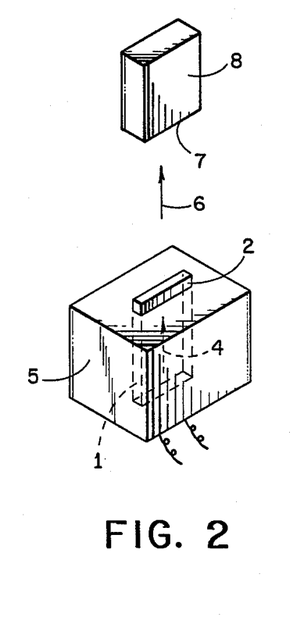
FIG. 2 is a perspective view of a device of the invention.

One embodiment of an optical measuring device of this invention is shown in simplified form in FIGS. 1 and 2. The device comprises a light source 1 for substantially uniformly illuminating a coating 2 on light-emitting surface 3 of the light source. Light source 1 projects a beam 4 of light having a longitudinal axis that coincides with the optical axis of the light source. Light source 1 is held in a fixed position in a lampholder 5.

Transmitted light beam 6 has a magnitude that is a function of the composition of the coating 2 under test. The transmitted beam 6 enters a sensing head 7 of light detector 8. The light detector 8 is usually a photodetector having an optical axis (not shown) coincident with the longitudinal axis of transmitted beam 6. In a preferred embodiment of the invention, at least a portion of the coating 2 is flat and the coincident axes of the light beam and photodetector are normal to the coating.

The beam of light from the light source interacts with the coating resulting in absorption or scattering of light or a combination of these phenomena. Ordinarily, the photodetector measures diffuse transmitted light. It will be understood that the light and coating can interact to produce fluorescence, and the resulting radiance can be sensed by the photodetector, although this is not a process that is commonly employed. Spectrally selective absorption and scattering of light by a transparent or translucent coating can produce color effects, and color intensity can be readily measured by the photodetector in this invention. Light diffusely transmitted from or through the coating can be compared with a similar nonabsorbing, nonscattering coating taken as a reference, although measurements of transmitted light before and after chemical reaction with the coating are generally more practical. In addition, measuring transmittance before and after chemical reaction provides a calibration that compensates for variations between light sources and between coatings that otherwise appear to be the same upon visual inspection.

Although specific terms are used in the following more detailed description of this invention, they refer only to particular embodiments of the invention selected for illustration and are not intended to limit the scope of the invention.

1. LIGAND

The term ligand is used to refer to body fluid constituents and medicaments or other substances present in such body fluids. The following exemplifies a number of such possible ligands.

The present assay element can be applied to the detection of any ligand for which there is a specific binding partner and, conversely, to the detection of the capacity of a liquid medium to bind a ligand (usually due to the presence of a binding partner for the ligand in the medium). The ligand usually is a peptide, polypeptide, protein, carbohydrate, glycoprotein, steroid, or other organic molecule for which a specific binding partner exists in biological systems or can be synthesized. The ligand, in functional terms, is usually selected from the group comprising antigens and antibodies thereto; haptens and antibodies thereto; and hormones, vitamins, metabolites and pharmacological agents, and their receptors and binding substances. Usually, the ligand is an immunologically-active polypeptide or protein of molecular weight between 1,000 and 10,000,000, such as an antibody or antigenic polypeptide or protein, or a hapten of molecular weight between 100 and 1,500.

Representative polypeptide ligands are angiotensin I and II, C-peptide, oxytocin, vasopressin, neurophysin, gastrin, secretin, bradykinin, and glucagon.

Representative protein ligands include the classes of protamines, mucoproteins, glycoproteins, globulins, albumins, scleroproteins, phosphoproteins, histones, lipoproteins, chromoproteins, and nucleoproteins. Examples of specific proteins are prealbumin, $\alpha_1$-lipoprotein, human serum albumin, $\alpha_1$-glycoprotein, transcortin, thyroxine binding globulin, haptoglobin, hemoglobin, myoglobin, ceruloplasmin, $\alpha_2$-lipoprotein, $\alpha_2$-macroglobulin, $\beta$-lipoprotein, erythropoietin, transferrin, homopexin, fibrinogen, the immunoglobins such as IgG, IgM, IgA, IgD, and IgE, and their fragments, e.g., $F_c$ and $F_{ab}$, complement factors, prolactin, blood clotting factors such as fibrinogen, thrombin and so forth, insulin, melanotropin, somatotropin, thyrotropin, follicle stimulating hormone, leutinizing hormone, gonadotropin, thyroid stimulating hormone, placental lactogen, intrinsic factor, transcobalamin, serum enzymes such as alkaline phosphates, cholinesterase, glutamic oxaloacetic transaminase, glutamic pyruvic transaminase, and uropepsin, endorphins, enkephalins, protamine, tissue antigens, bacterial antigens, and viral antigens such as hepatitis associated antigens (e.g., $HB_s$, Ag, $HB_2A_g$ and $HB_eAg$).

Representative hapten ligands include the general classes of drugs, metabolites, hormones, vitamins, and the like organic compounds. Haptenic hormones include thyroxine and triiodothyronine. Vitamins include vitamins A, B, e.g., $B_{12}$, C, D, E and X, folic acid and thiamine. Drugs include antibiotics such as aminoglycosides, e.g., gentamicin, tobramycin, amikacin, sisomicin, kanamycin, and netilmicin, penicillin, tetracycline, terramycin, chloromycetin, and actinomycetin; nucleosides and nucleotides such as adenosine diphosphate (ADP), adenosine triphosphate (ATP), flavin mononucleotide (FMN), nicotinamide adenine dinucleotide (NAD) and its phosphate derivative (NADP), thymidine, guanosine and adenosine; prostaglandins, steroids such as the estrogens, e.g., estriol and estradiol, sterogens, androgens, digoxin, digitoxin, and adrenocortical steroids; and others such as phenobarbital, phenytoin, primidone, ethosuximide, carbamazepin, valproate, theophylline caffeine, propranolol, procainamide, quinidine, amitryptilane, cortisol, desipramine, disopyramide, doxepin, doxorubicin, nortryptiline, methotrexate, imipramine, lidocaine, procainamide, N-acetylprocainamide, the amphetamines, the catecholamines, and the antihistamines.

The liquid medium to be assayed can be a naturally occurring or artificially formed liquid suspected to contain the ligand, and usually is a biological fluid or a dilution thereof. Biological fluids that can be assayed include serum, plasma, urine, saliva, and amniotic and cerebrospinal fluids.

2. COATING

The coating is provided directly on the light-emitting surface of the light source without any intervening solid, liquid or gaseous layers. This ensures that light from the light source will not be diffused before the light illuminates the coating.

The coating can be transparent or translucent so that light from the source is diffusely transmitted to the photodetector. The coating can be self-supporting or unsupported, i.e., a coating that is not capable of maintaining dimensional stability when removed from the light source.

The coating is absorbent, that is, it is capable of being wetted by and absorbing the liquid test sample containing the ligand or the reagent system for the ligand. Preferably the coating is hydrophilic or permeable to liquids that contain the ligand under test. Most preferably, the coating is water permeable.

The coating on the light source can be derived from a fluid coating composition containing the ligand or a reagent system chemically reactive with the ligand. The coating composition can be applied to the light source using conventional techniques, such as dipping, brushing, spraying, roller coating or extruding the coating on the light-emitting surface of the source. The coating on the light source can be dried in air at ambient temperature of about 20° C. A slightly elevated temperature can be employed if necessary to speed drying or to cure the coating.

The fluid coating composition can be in the form of a solution, dispersion, or suspension. A solvent, such as water or an organnic compound, can be included in the composition to facilitate application of the composition to the light source. The composition can contain other coating aids, such as one or more of the following materials: defoamer, dispersing agent, binder, gum, wax, drying agent, lubricant, opacifier, plasticizer, hydrophobic agent, release agent, suspending agent, thickner or surface wetting agent. The amount of each ingredient required for a particular application can be determined with a minimum of experimentation.

A binder can be incorporated in the coating composition to improve adhesion to the light source. A binder of natural or synthetic origin can be employed for this purpose. Examples of suitable binders include gelatin; cellulose derivatives, such as cellulose nitrate, ethyl cellulose and methyl cellulose; or a hydroxyalkyl cellulose, such as hydroyethyl cellulose and hydroxypropyl cellulose; or a cellulose ester, such as cellulose acetate, or an ester or mixed ester with other fatty acids; or a cellulose ether. Vinyl compounds can also be employed as binders in the coating composition. Examples of suitable vinyl compounds are polyethylene, polypropylene, ethylene-vinyl acetate copolymer, polyvinyl chloride, polyvinyl fluoride, poly(ethylene oxide), poly(propylene oxide), polyvinyl alcohol, polyvinyl acetate, and vinyl chloride—vinyl acetate copolymers.

The thickness of the coating and its degree of permeability are widely variable and depend on actual usage. Dry thicknesses of from about 10 microns to about 750 microns, preferably from 50 to about 600 microns, have been convenient, although more widely varying thickness may be preferable in certain circumstances. The particularly preferred dry thickness of the coating is about 150 to about 500 microns.

It may be advantageous to incorporate one or more surfactant materials, such as anionic and nonionic surfactant materials, in the coating. A surfactant can enhance coatability of formulations and enhance the extent and range of wetting in layers that are not easily wetted by liquid samples in the absence of an aid.

The reagent system is chemically reactive with the ligand to produce a change in transmittance of light after the reagent is reacted with the ligand. The reagent system can contain a suitable indicator. Thus, if the coating is to be responsive to glucose, it can contain a glucose oxidase enzyme, a peroxidase enzyme and o-toluidine. Such a reagent system turns blue when contacted with a liquid sample containing glucose.

Reagent compositions are also known for blood, plasma or serum ligands, such as ascorbic acid, bile acids, bilirubin, cholesterol, creatinine, lactic acid, phospholipids, triglycerides, urea nitrogen (BUN) and uric acid, and can be incorporated in the coating. Also important is the determination of blood chemistry enzyme ligands such as amylase, cholinesterase, creatine phosphokinase (CPK), the dehydrogenases (hydroxybutyric, isocitric, lactic and malic), lipase, phenylalanine, the transaminases (glutamic oxaloacetic and glutamic pyruvic), acid and alkaline phosphatases, gammal-glutamyl transpeptidase, leucine aminopeptidase and the erythrocyte enzymes (glucose-6-phosphate dehydrogenase; 6-phosphogluconate dehydrogenase; glutathione reductase; and pyruvate kinase).

Likewise, reagent compositions for urine chemistry determinations can be employed in the coating. In the field of urine chemistry such ligands generally include ascorbic acid, albumin, creatine, creatinine, glucose, bile acids, bilirubin, protein, ketones, occult blood, nitrite, amylase and phenylpyruvic acid.

The selection of the proper reagent composition and indicator is well within the skill of the art and is easily determined in accordance with known analytical chemistry techniques.

The coating can be comprised of areas having different reagent systems. Thus, the coating can be suitable for carrying out tests for more than one constituent in a particular liquid sample.

3. SUPPORT MATRIX

The coating can contain a solid support matrix to improve properties and handleability. The support matrix can be a solid, continuous or discontinuous material capable of passing light from the light source. Thus, the support matrix is transparent or translucent. The support matrix can also be rigid or flexible. Woven and nonwoven webs and mesh structures are suitable for use as support matrices. The webs can be comprised of fibers or threads of natural or synthetic origin. Ordinarily, the support matrix will be inert; that is, the matrix will not react with the ligand or the reagent system for the ligand. Nevertheless, it will be understood that a reactive support matrix can be employed in the coating.

The support matrix mainly functions as a skeleton to impart dimensional stability to the coating. Thus, the coating can be on an exposed surface of the matrix or the coating can completely cover the matrix. In the preferred embodiment of the invention, the coating uniformly covers the matrix and fills the major portion of interstices the matrix may contain. Since the coating contains the reagent system responsive to the ligand, the reagent system will be substantially uniformly distributed throughout the matrix in the preferred embodiment.

When a support matrix is incorporated in the coating, it is preferable that the support matrix be wettable by the test sample. It is particularly preferred that the matrix be liquid permeable so that the ligand can react with the reagent throughout the matrix. It is also preferred that the support matrix be comprised of a hydrophilic material or a material that is rendered hydrophilic by suitable treatment. In the case where the liquid test sample is aqueous, both synthetic and natural paper-like materials can be employed. The support matrix can be comprised of filter paper, cloth, felt, porous ceramic, woven or matted glass fibers, polyamide fibers, and similar materials.

The support matrix can be comprised of a multiplicity of layers, for example, a plurality of reagent layers, such as a first reagent layer and a second reagent layer; a detecting layer; a radiation blocking layer; a sample spreading layer; and the like.

The support matrix can be a multilayer element containing absorbent fibers impregnated with one or more reagents, typically including a color former. Upon contact with a test liquid, analyte passes into the fibrous support to generate color in an amount related to the concentration of analyte. A membrane can be included to prevent passage and absorption of certain interfering components, such as red blood cells, that could impair accurate reading of the color. The support matrix can include a spreading layer to obtain an apparent uniform concentration of analyte, other appropriate sample constituent or analyte product.

Where the support matrix comprises multiple layers, the layers can be maintained in laminar relationship by adhesives which permit fluid passage between layers. It is not always necessary to employ adhesive to adhere one reagent layer to another. An integral support matrix can be prepared using film formers, with layers separately preformed and laminated to form the overall element.

The solid support matrix can be derived from a so-called "dip-and-read" type reagent strip. Test strips of this type have become commonplace in the analysis of various types of samples, particularly biological fluids. Test strips designed for detecting clinically significant substances in biological fluids, such as serum and urine, are especially useful.

Reagent strips can be used to monitor numerous physiological functions merely by dipping a strip into a sample of body fluid, such as urine, and observing a detectable response, such as a change in color or a change in the amount of light absorbed by the strip. Reagent compositions found in such test strips interact with the constituent or constituents to be determined by direct chemical reaction and are applied to the detection of substances that may be present in liquid samples in very small amounts. Some reagent test strips and their reactant systems are set forth in U.S. Pat. Nos. 3,992,158, 3,802,842; 3,123,443; 3,212,855; 3,814,668; 3,164,534; 2,981,606; 3,298,789; 3,092,465 and 2,981,606, the entire disclosures of which are relied upon and incorporated by reference herein.

Many of the known reagent test strips have more than one reagent-bearing carrier matrix or layer, and strips of this type can be employed as the solid support matrix in this invention. Thus, a reagent strip can contain tests for more than one constituent in a particular liquid sample. For example, a single reagent strip can consist of a reagent-bearing carrier matrix responsive to glucose in urine, and another carrier layer spaced from the first but adjacent thereto and responsive to ketones, such as acetonacetate. Another reagent strip contains eight adjacent reagent-incorporated matrices and provides analytical measurements of pH, protein, glucose, ketones, bilirubin, occult blood, nitrite and urobilinogen.

Reagent test strips can be made by many different techniques, such as by impregnating paper layers, by printing or spraying the reagent composition onto a layer of the carrier material, or by forming films which are solidified.

4. LIGHT SOURCE

The light source employed in practicing the invention should be capable of producing a beam of light in the region of the electromagnetic spectrum to which the coating and the detector respond. Thus, the light source should be selected to emit light having a wavelength that is readily absorbed by the coating. Light in the visible region of the spectrum is generally employed. The light source can be selected to produce light having a broad range of wavelengths or the light source can produce light within a narrow wavelength range. Typically, the light source will be capable of emitting light having a wavelength of about 400 nanometers (nm) to about 700 nm, preferably above about 500 nm. The wavelength should be at or near the wavelength of maximum absorbance of the species being detected. In the preferred embodiment of the invention the light source produces light of substantially one wavelength, i.e., monochromatic light, within these wavelength ranges.

The use of light-emitting semiconductor devices, such as light-emitting diodes (LEDs), has been found to be particularly advantageous in this invention. Light-emitting diodes capable of emitting diffuse, monochromatic light are commercially available in the wavelength ranges previously described. The light-emitting diodes are of low cost, have low power requirements and high radiance. Exemplary LEDs are those based on GaAlAs, GaP, GaAsP/GaP and equivalent chip materials.

The output from the light source should be stable in order to obtain accurate and reliable optical measurements because changes in output of the light source are indistinguishable to the detector from changes in light transmitted through the coating. The light is generated by feeding to the light source electric current having a duration sufficient to obtain the stable, reproducible output. The duration will depend upon the nature and operating characteristics of the light source and the speed of response of other components of the device. Current control can be accomplished by switching and timing means operable such that the light source is energized and deenergized at predetermined times. For instance, stable output can generally be obtained with LEDs energized for about 100 to about 300 milliseconds at about 20 to about 25 milliamps input current.

Heat is generated in the light source and the heat can adversely affect the stability and reproducibility of the output from the source. In addition, heat can adversely affect the properties of the coating or the ingredients in the coating. In order to minimize the adverse effects of heat, the duration of the charge to the light source will typically be reduced at the higher input currents.

The intensity of the light beam from the light source can be varied over a wide range. Ordinarily, the desired magnitude of the energy transmitted from the coating will be established based upon the sensitivity of the detector and nature of the circuitry for processing the signal from the detector. The intensity of the light beam should be adequate to provide a transmitted beam under the test conditions so that it is possible to discriminate between changes in concentration in the coating. The intensity of the light beam can be controlled by regulating input current to the source, which in turn will vary depending on the nature of the light source and its operating characteristics.

5. LIGHT DETECTOR

The photodetector receives light passed through or from the coating and is selected so that it will respond over the range of wavelengths of light transmitted through or from the coating under the test conditions. The photodetector should have high sensitivity to the light and fast response time. In the preferred device of this invention, the photodetector is responsive to light having wavelengths in the range of about 400 to about 700 nm at about 25° C. The photodetector is preferably a silicon photodiode operating in the photovoltaic mode.

The light detector is positioned so that its optical axis substantially coincides with the longitudinal axis of the transmitted beam. This will ensure efficient collection of the transmitted beam by the detector. The detector will generally be placed as close as practically possible to the surface of the coating under test in order to minimize transmission losses as the transmitted beam travels between the coating and the detector. In some cases, however, the detector can be spaced farther away from the coating by selecting a detector having a larger viewing area or by incorporating light guiding means, e.g. fiber optics, between the coating and detector. The coating or light source can be moved to permit scanning of the surface or the determination of transmittance from different areas of the coating. The photodetector can be moved to permit scanning of the surface of the coating. Similarly, movement of the detector can be coordinated with movement of the coating.

It will be understood that the invention can also be practiced with a light source capable of producing polychromatic light and means for separating all but the light of a limited wavelength from the transmitted beam so that diffuse light having the characteristics previously described activates the detector. This can be accomplished, for example, by employing a monochromatic detector. Alternatively, a suitable optical filter can be interposed in the path of the transmitted beam between the coating and the detector. This can typically be accomplished with a tungsten lamp and a suitable filter placed in front of the detector in the path of the transmitted beam.

Optical filters of the type well known in the art can be employed in the device of the invention to alter, modulate or more precisely control the spectral radiant energy. Neutral, polarizing or color filters can be incorporated in the apparatus as needed. Absorption filters and interference filters can be selected from among commercially available filters to produce a particular effect.

It will be understood that the light transmitted through the coating can be reflected or refracted after exiting the coating and before entering the photodetector, although there is usually no reason for doing so. A mirror or lens or a system of mirrors and lenses can be employed for this purpose.

6. SIGNAL PROCESSING

The electrical signal produced by the photodetector can be processed using conventional techniques. An electronic unit for signal processing and data display can be employed for this purpose. For example, a photodiode that produces a current can be used to feed an operational amplifier used as a high gain current or voltage converter. The photodiode and operational amplifier can be connected such that higher levels of transmitted light produce less positive voltage levels. Analog to digital conversion of voltage output from the operational amplifier can be accomplished in an analog to digital converter. The resulting signal can then be reported using a conventional display device.

The test device of the invention is advantageously used by inserting the coated lamp in the device. The lamp is energized and the light transmitted from the coating is measured. This measurement is the "blank" or reference value ($T_{ref}$). The coating is then contacted with the ligand or a medium thought to contain the ligand. In the event the ligand is in the coating, the coating is contacted with a reagent responsive to the ligand. Reaction time sufficient for the ligand and reagent to chemically react is provided. The lamp is again energized and the light transmitted through or from the coating is measured. This measurement is the sample value ($T_{sam}$). The measured light values are then compared with a standard to determine the presence of the ligand or the concentration of the ligand, if present. It will be understood that $T_{ref}$ can be greater than $T_{sam}$ or $T_{sam}$ can be greater than $T_{ref}$. The latter occurs when the light transmittance of the coating increases after the coating is contacted with a fluid under test. In the case of a glucose reagent coating, the coating is generally selected and formulated so that $T_{ref}$ is about 50% to about 600% of $T_{sam}$.

It has been found that $T_{ref}$ and $T_{sam}$ for a given coating can be converted to a ratio, namely, $T_{ref}/T_{sam}$, and that the ratio can be compared with standad ratios calculated from known coating compositions. The calculated ratio provides good separation of values between coatings containing different concentrations of ligand. In addition, the calculated ratio appears to minimize the differences in measurements caused by variations in light sources and the quality of coatings made with the same coating composition for repeat measurements.

Even better separation of measurements can be obtained by comparing the natural logarithm (ln) of the calculated $T_{ref}/T_{sam}$ ratios with the corresponding ln of standard ratios for known coating compositions. The ln values appear to further minimize the differences in measurements caused by variations in light sources and the quality of the coating.

This invention will be more fully understood by reference to the following Examples. All parts, proportions, ratios and percentages are by weight unless otherwise indicated.

EXAMPLES

Apparatus Employed in the Examples

A device for determining sample concentration by measuring transmittance of light through a translucent coating was assembled from the following components.

A model HLMP-0301 rectangular light-emitting diode (LED) was obtained from Hewlett Packard. The LED had a flat face through which light having a peak wavelength of 635 nm was emitted. The LED was mounted in a rigid lampholder constructed to permit easy removal and replacement of the lamp.

A photodetector sensitive to light from 500 to 700 nm was rigidly mounted to receive light from the LED. The photodetector had a built-in meter to indicate light level. A filter was interposed between the LED and photodetector to limit the wavelength of light reaching the photodetector to about 635 nm.

An AC/DC convertor provided with a rheostat was connected to the LED. The convertor was used to provide DC current to the LED. The rheostat made it possible to vary the electric current to the lamp for experimental purposes. A Beckman 3020B multimeter was connected to the LED to monitor current flow.

Example 1

Reagent Coated Light Source—Translucent Film on LED

A translucent film in the form of a glucose reagent paper was used in this Example. The translucent film was a chemically impregnated, glucose sensitive paper made by Ames Division, Miles Laboratories. The reagent paper contained glucose oxidase, peroxidase and an indicator, tetramethylbenzidine. An inert dye and buffer were also present. The paper had a pressure sensitive adhesive attached to one side.

The LED was mounted in the holder by insertion from the rear of the holder. The flat, leading face of the LED just fit in a small opening in the front of the holder. The leading face of the LED was positioned to be flush with the front surface of the holder, and the LED was visible through an opening in the holder. This opening was covered by a piece of the reagent paper measuring approximately 0.5 cm×0.5 cm.

Application of direct current caused the LED to emit light. Some of the light passed through the translucent film by forward scattering. This transmitted light was measured via the photodetector. With a dry film in place and with a LED current of about 20 mA, the gain of the photodetector was adjusted to give a value which fell in the linear range of the detector. Once set, it was not necessary to change the current and gain settings.

The light level transmitted by the dry reagent paper was measured. This measurement was the reference signal ($T_{ref}$). A drop of a glucose-containing sample was placed on the film coating the flat face of the LED. After a reaction time of 30 seconds, the light transmitted by the translucent film was read. This was the sample signal ($T_{sam}$). The reacted paper was removed, and a new reagent paper put in place. This procedure was repeated by placing solutions containing 0 to 500 mg/dL glucose on specimens of the reactive film. Two measurements were made on each solution.

The actual photodetector measurements for each reference and each sample were summarized in TABLE I. The TABLE also includes the calculated ratio of reference to sample photodetector measurements for each solution tested.

TABLE I
ACTUAL PHOTODETECTOR VALUES FOR LIGHT TRANSMITTED THROUGH COATED LIGHT SOURCE (TRANSLUCENT FILM ON LED)

| GLUCOSE CONC. mg/dL | $T_{ref}$ | $T_{sam}$ | $T_{ref}/T_{sam}$ |
|---|---|---|---|
| 0 | 60 | 121 | 0.50 |
| 0 | 60 | 122 | 0.49 |
| 12.5 | 60 | 91 | 0.66 |
| 12.5 | 60 | 88 | 0.68 |
| 25 | 168 | 172 | 0.98 |
| 25 | 100 | 109 | 0.92 |
| 50 | 158 | 111 | 1.42 |
| 50 | 158 | 116 | 1.36 |
| 50 | 158 | 111 | 1.42 |
| 100 | 155 | 60 | 2.58 |
| 100 | 156 | 60 | 2.60 |
| 250 | 160 | 31 | 5.16 |
| 250 | 160 | 32 | 5.00 |
| 500 | 154 | 27 | 5.70 |
| 500 | 121 | 20 | 6.05 |
| 500 | 120 | 20 | 6.00 |
| 500 | 115 | 20 | 5.75 |

TABLE I shows that even when the reference and sample values are very different for replicate samples, the ratio compensates for these differences. For example, at 25 mg/dL glucose, a portion of the light emitting surface of the LED used for the second test was intentionally masked thereby reducing $T_{ref}$. Although there was a substantial reduction in $T_{ref}$ to 100 from 168, the ratio $T_{ref}/T_{sam}$ was not appreciably affected, i.e. 0.98 vs. 0.92.

At 500 mg/dL glucose, the same type LEDs were used for the second and third measurements, but different LEDs were used for the first and fourth measurements. TABLE I shows that the $T_{ref}$ values significantly varied for the different types of LEDs, but the ratios $T_{ref}/T_{sam}$ were not appreciably different. It is therefore possible that variations in output among LEDs can be compensated for by computing and comparing $T_{ref}/T_{sam}$ ratios.

Variations in the uniformity or thickness of a coating should not be so great that the light transmitted from or through the coating is substantially reduced. Preferably, the coating on the LED is substantially uniform in thickness and composition. Nevertheless, some variation in coating uniformity can be tolerated because coating to coating differences can be compensated for by computing and comparing $T_{ref}/T_{sam}$ values.

In addition to calculating the ratio of reference to sample photodetector measurements for each solution, the natural logarithm of each ratio was determined. The choice of a log function was empirical, but a theoretical relationship between log function and the concentration of absorbing species on the film can be derived from Kubelka-Munk equations. The results are set forth in TABLE II.

TABLE II
RATIO OF TRANSMITTED LIGHT THROUGH REAGENT COATED LIGHT SOURCE (TRANSLUCENT FILM ON LED)

| GLUCOSE CONC. mg/dL | $(T_{ref}/T_{sam})$ | $\ln(T_{ref}/T_{sam})$ |
|---|---|---|
| 0 | 0.50 | −0.70 |
| 0 | 0.49 | −0.71 |
| 12.5 | 0.66 | −0.42 |
| 12.5 | 0.68 | −0.38 |
| 25 | 0.98 | −0.01 |
| 25 | 0.92 | −0.09 |
| 50 | 1.42 | 0.35 |
| 50 | 1.36 | 0.31 |
| 50 | 1.42 | 0.35 |
| 100 | 2.58 | 0.94 |
| 100 | 2.60 | 0.96 |
| 250 | 5.16 | 1.64 |
| 250 | 5.00 | 1.61 |
| 500 | 5.70 | 1.74 |
| 500 | 6.05 | 1.80 |
| 500 | 6.00 | 1.79 |

TABLE II shows good agreement with replicate measurements; the data demonstrate good reproducibility with the invention. Separation at 12.5 mg/dL indicates extremely good sensitivity.

Figure 3:
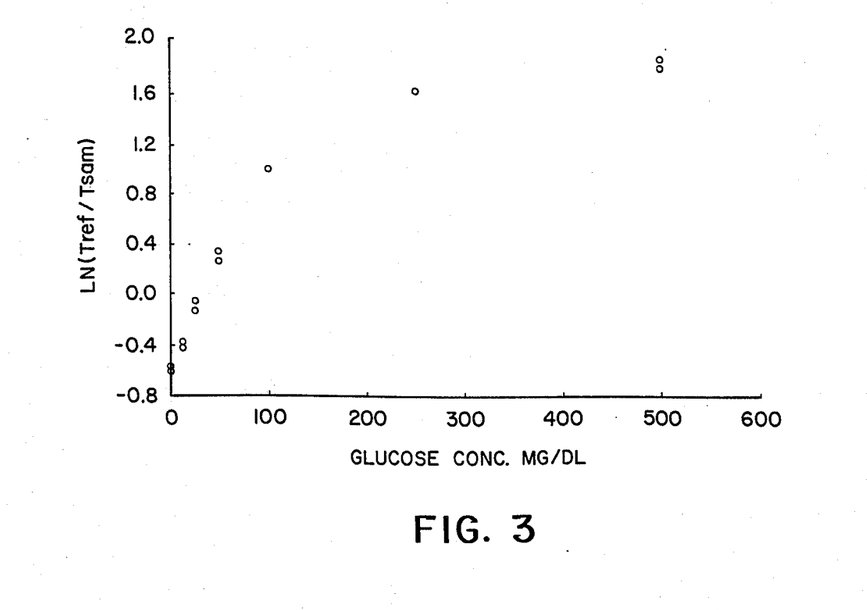
FIG. 3 is a plot of the ratio of photodetector measurements versus glucose concentration for experiments described in Example 1 using a translucent film coated on a LED.

The natural log of each ratio is plotted as a function of glucose concentration in FIG. 3. The plot demonstrates good separation of values, especially at low concentrations.

Figure 4:
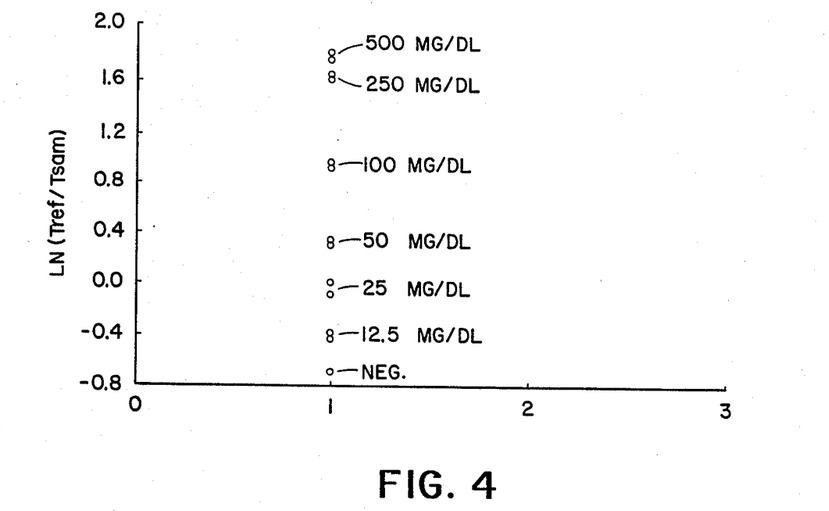
FIG. 4 is a plot similar to FIG. 3, except that all of the ratios calculated in Example 1 are plotted on a vertical axis to emphasize the separation between measurements made at different glucose concentrations.

The same function is represented again in FIG. 4 with the various concentrations represented on a single vertical line to demonstrate the separation between glucose levels. Good separation between glucose levels is evident from the Figure.

Figure 5:
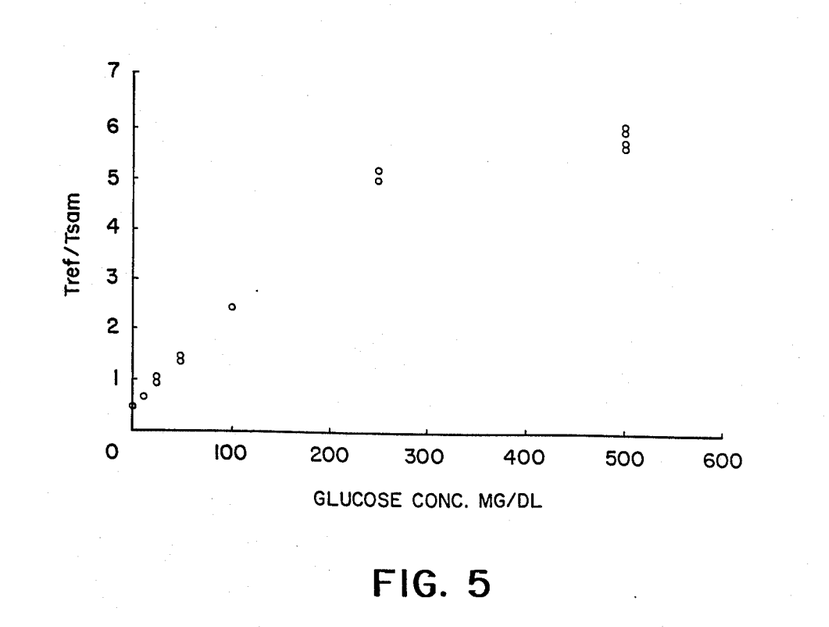
FIG. 5 is a graph of the natural logarithm as a function of glucose concentration for each ratio calculated in Example 1.
Figure 6:
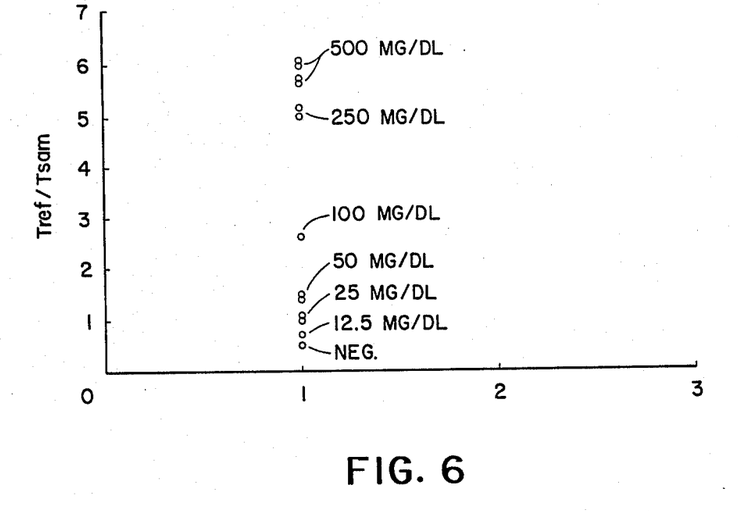
FIG. 6 is a plot similar to FIG. 5, except that all of the natural logarithms are plotted on a vertical axis to emphasize the separation between measurements made at different glucose concentrations.

The ratio values from TABLE I are plotted as a function of glucose concentration in FIG. 5, and again with all concentrations on a single vertical line in FIG. 6. The separation between the concentration levels is not as good for the ratio plot of FIGS. 5 and 6 as in the natural logarithm of the ratio plot of FIGS. 3 and 4. That is, of the two algorithms, the ln function is preferable for the glucose reagent paper.

Example 2

Reagent Coated Light Source—Glucose Coating on LED

In this Example a LED with a glucose coating on the light-emitting surface of the lamp was used.

A coating composition was prepared by mixing the following ingredients to obtain a viscous, light brown material:

0.5 ml: Water soluble polymer; Borchigel DP 40, Bayer A. G., Leverkusen, West Germany; 40% stock solution;
  0.1 ml: Glucose oxidase L 5000, Miles Laboratories, Elkhart, Ind.; 5000 IU/ml;
  0.1 ml: Peroxidase; 60 mg/ml solution; 68 IU/mg;
  0.5 ml: Tetramethylbenzidine; 0.5 g/ml solution.

The lamp was coated by applying about 10 μL of the coating composition onto the flat, light-emitting face of the LED. The coated surface was air dried for 1 hour. The coating was further dried at a higher temperature by placing the LED in an oven at 50° C. for 25 minutes.

The LED, with the leading face already coated, was carefully inserted from the rear of the lampholder. With the LED positioned flush with the front surface of the holder, the coated face of the LED was visible through a small opening in the front of the holder.

The LED current setting and the photodetector gain setting were adjusted to give a photodetector value within the linear range of the photodetector. Once set, the current and gain settings were not changed.

The light level for the dry coating was measured. This was the reference signal ($T_{ref}$). A drop of an aqueous glucose solution was placed on the coating. After a reaction time of 30 seconds, a new light level was read. This was the sample signal ($T_{sam}$). The reacted LED was then replaced with a new, coated LED.

The procedure was repeated with solutions containing 0 to 1000 mg/dL glucose. Repeat measurements were made on some of the coating solutions. The ratio of the reference signal to the sample signal was calculated for each solution assayed. The actual photodetector measurements and the calculated ratios are summarized in TABLE III.

TABLE III
ACTUAL PHOTODETECTOR VALUES FOR LIGHT TRANSMITTED THROUGH COATED LIGHT SOURCE (GLUCOSE COATING ON LED)

| GLUCOSE CONC. mg/dL | $T_{ref}$ | $T_{sam}$ | $T_{ref}/T_{sam}$ |
|---|---|---|---|
| 0 | — | — | — |
| 25 | 56 | 34 | 1.65 |
| 25 | 146 | 80 | 1.82 |
| 50 | 95 | 52 | 1.83 |
| 50 | 94 | 46 | 2.04 |
| 100 | 105 | 28 | 3.75 |
| 250 | 144 | 42 | 3.43 |
| 250 | 99 | 25 | 3.96 |
| 500 | 113 | 22 | 5.14 |
| 1000 | 122 | 30 | 4.07 |
| 1000 | 100 | 18 | 5.56 |
| 1000 | 146 | 28 | 5.21 |

The coated films were reactive. However, they had a tendency to dissolve in the sample or float off the LED surface. These shortcomings impacted on the precision of the results. Examination of the actual photometer values in TABLE III shows that measurements with a coated LED are not as precise as the data obtained with a translucent film. The primary reason is the visually observed instability of the coatings. However, the use of a ratio compensates quite well for variation in lamp output. For example, the replicate transmittance values at 25, 250 and 1000 mg/dL glucose are variant, but the ratios are relatively invariant.

The natural logarithms for the ratios in TABLE III were determined and the results are summarized in TABLE IV. As with the translucent film on the LED, the ratio values and ln of the glucose coating increase with increasing glucose concentration.

TABLE IV
RATIO OF TRANSMITTED LIGHT THROUGH REAGENT COATED LIGHT SOURCE (GLUCOSE COATING ON LED)

| GLUCOSE CONC. mg/dL | $T_{ref}/T_{sam}$ | $\ln(T_{ref}/T_{sam})$ |
|---|---|---|
| 0 | — | — |
| 25 | 1.65 | 0.50 |
| 25 | 1.82 | 0.60 |

TABLE IV-continued
RATIO OF TRANSMITTED LIGHT THROUGH REAGENT COATED LIGHT SOURCE (GLUCOSE COATING ON LED)

| GLUCOSE CONC. mg/dL | $T_{ref}/T_{sam}$ | $\ln(T_{ref}/T_{sam})$ |
|---|---|---|
| 50 | 1.83 | 0.60 |
| 50 | 2.04 | 0.71 |
| 100 | 3.75 | 1.32 |
| 250 | 3.43 | 1.23 |
| 250 | 3.96 | 1.38 |
| 500 | 5.14 | 1.64 |
| 1000 | 4.07 | 1.40 |
| 1000 | 5.56 | 1.71 |
| 1000 | 5.21 | 1.65 |

Figure 7:
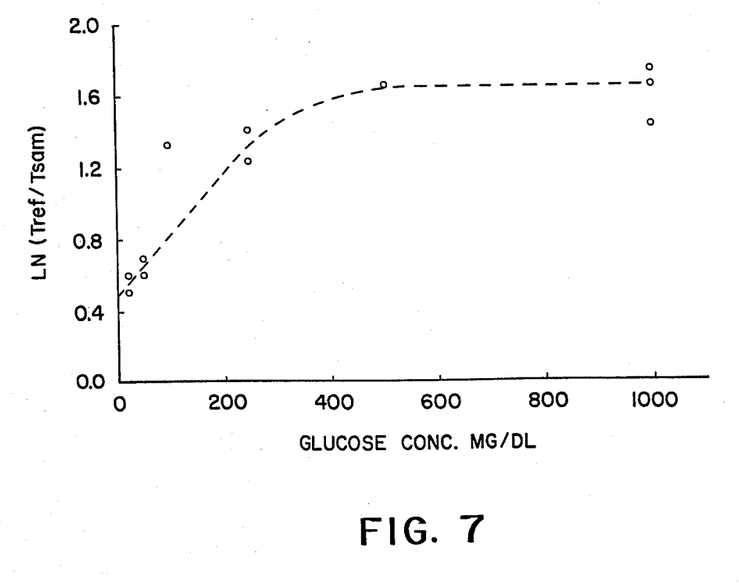
FIG. 7 is a plot of the natural logarithms of ratios of photodetector measurements as a function of glucose concentrations for experiments described in Example 2 using a glucose coating on a LED.

A plot of the natural logarithms of the ratio values as a function of glucose concentration is shown in FIG. 7. The plot demonstrates the increase in the log-ratio value with glucose concentration.

Example 3

Reagent Coated Light Source—Fluorescent Reagent Paper

A fluorescent reagent paper is made by dipping filter paper in a solution containing a fluorophore. The fluorophore can be pyrene, which emits light of wavelength above 400 nm, maximum about 420 nm, when excited with ultraviolet radiation of wavelength 316 nm. At high pyrene concentration, a second larger fluorescence peak occurs at longer wavelengths with a maximum at about 480 nm.

The amount of pyrene on the paper is varied by the use of different concentrations of pyrene solution as follows:

$1 \times 10^{-2}$M: 0.202 g of Pyrene (M.W. 202)/100 mL of cyclohexane.
$1 \times 10^{-3}$M: Serial dilution of above in cyclohexane.
$1 \times 10^{-4}$M: Serial dilution of above in cyclohexane.
$1 \times 10^{-5}$M: Serial dilution of above in cyclohexane.
$1 \times 10^{-6}$M: Serial dilution of above in cyclohexane.

Ultraviolet light is brought to the paper by means of a source capable of emitting uv radiation and a light pipe, such as a fiber optic bundle. One end of the fiber optic bundle receives the uv light and guides it to the other end, which is positioned in a holder. The end of the light guide is visible through an opening in the holder.

A piece of dry reagent paper is placed over the opening in the holder in such a way that it will be illuminated by uv light from the light guide.

The fluorescence emission is measured with a photodetector. A cut-off filter or a band pass filter (420 nm or 480 nm) is placed in the light path between the reagent paper and the detector to eliminate uv excitation radiation (316 nm).

The uv radiation is turned on. The light emitted from the dry pad is measured. This is the reference signal ($T_{ref}$). A drop of pyrene solution is placed on the pad. The new light level is read within about 15 seconds. This is the sample signal ($T_{sam}$). The paper is removed and a new dry pad put in place.

Fluorescence intensity increases with increasing pyrene concentration. The ratio obtained by dividing the dry pad reference value ($T_{ref}$) by the sample signal value ($T_{sam}$) represents a quantitative relationship between measured fluorescence and pyrene concentration.

In this Example, the fluorophore is introduced to the system via solutions of varying concentration to demonstrate how the system can be used to measure fluorophore concentration. In some systems, fluorophore is produced in situ; for example, by enzyme cleavage to produce a fluorescent compound, which is either non-fluorescent before enzyme cleavage or which fluoresces at a different wavelength. In such systems, the coated light source method permits the quantitation of the fluorophore produced, and by extension, it also permits quantitation of the reaction(s) that produce the fluorophore in situ.

In summary, this invention provides a method and a device for making rapid, accurate and reproducible optical measurements on a specimen under test by direct illumination of the specimen. The device minimizes the amount of illumination dissipated or lost between the light source and the specimen. The device provides optical measurements that are not sensitive to changes in the orientation of the specimen in a specimen holder and not susceptible to variations in the distance between the light source and the specimen as in prior art devices.

What is claimed is:

1. A light-emitting diode consisting of
   a light-emitting diode end surface through which light from the diode can pass;
   a liquid permeable, light-transmitting coating on the end surface of the diode;
   a reagent composition for a ligand from a body fluid, wherein the reagent composition is contained in the coating and is chemically reactive with the ligand to produce a change in transmittance of light by the coating.

2. Light-emitting diode according to claim 1, wherein said end surface of the diode is substantially flat.

3. Light-emitting diode according to claim 1, wherein the coating also contains the ligand.

4. Light-emitting diode according to claim 1, wherein the coating contains the product of the reaction of ligand and reagent composition.

5. Light-emitting diode according to claim 1, wherein the reagent in the coating comprises glucose oxidase, peroxidase and a color indicator.

6. Light-emitting diode according to claim 5, wherein the indicator is tetramethylbenzidine.

7. Light-emitting diode according to claim 6, wherein the coating contains a solid, transparent or translucent, liquid permeable support matrix.

8. A method for determining the presence or concentration of a ligand in a specimen by measuring transmission of light in a device comprising light source means for illuminating the specimen and means for measuring light from the specimen, wherein the method comprises
   providing a transparent or translucent coating on an end surface of the light source through which light from the light source passes, wherein the coating contains a reagent that displays chemical reactivity with a ligand by a change in optical characteristics;
   measuring light from the light source transmitted from the coating to said measuring means;
   applying a liquid specimen containing the ligand onto the coating;
   allowing sufficient time to react substantially all of the ligand in the liquid specimen to form an optically discernible product; and
   measuring light from the light source transmitted from the coating containing the reaction product to said measuring means.

9. Method according to claim 8, wherein the coating contains a solid, transparent or translucent, liquid permeable, support matrix.

10. Method according to claim 9, wherein the support matrix is a translucent nonwoven paper web.

11. Method according to claim 10, wherein the reagent in the coating comprises glucose oxidase, peroxidase and a color indicator.

12. Method according to claim 11, wherein the indicator is tetramethylbenzidine.